US009572922B2

(12) United States Patent
Leonard

(10) Patent No.: US 9,572,922 B2
(45) Date of Patent: Feb. 21, 2017

(54) INVENTIVE DIABETIC SYSTEMS, TOOLS, KITS, AND SUPPLIES FOR BETTER DIABETIC LIVING AND MOBILITY

(71) Applicant: Larry Leonard, Edmonds, WA (US)

(72) Inventor: Larry Leonard, Edmonds, WA (US)

( * ) Notice: Subject to any disclaimer, the term of this patent is extended or adjusted under 35 U.S.C. 154(b) by 998 days.

(21) Appl. No.: 13/725,921

(22) Filed: Dec. 21, 2012

(65) Prior Publication Data

US 2014/0180243 A1    Jun. 26, 2014

(51) Int. Cl.
*B65D 69/00* (2006.01)
*A61M 5/00* (2006.01)
*A61M 5/178* (2006.01)

(52) U.S. Cl.
CPC ............ *A61M 5/003* (2013.01); *A61M 5/178* (2013.01)

(58) Field of Classification Search
CPC ........ A61F 17/00; A61M 5/3129; A61M 5/24; A61M 5/178; A61M 5/002; A61M 5/003
USPC ........................................ 206/570, 571, 828
See application file for complete search history.

(56) References Cited

U.S. PATENT DOCUMENTS

| | | |
|---|---|---|
| 1,995,799 A | 8/1932 | Doniger |
| 2,038,319 A | 4/1936 | Stanley |
| 3,786,510 A * | 1/1974 | Hodges .............. A61B 5/14532 206/232 |
| 3,814,668 A | 6/1974 | Blake |
| 3,841,329 A | 10/1974 | Killinger |
| 4,061,144 A | 12/1977 | Strickman |
| 4,250,998 A | 2/1981 | Taylor |
| 4,424,720 A | 1/1984 | Bucchianeri |
| 4,429,793 A | 2/1984 | Ehmann |
| 4,444,560 A | 4/1984 | Jacklich |
| 4,446,970 A * | 5/1984 | Further ................. A61M 5/002 206/223 |
| 4,516,967 A | 5/1985 | Kopfer |
| 4,561,856 A | 12/1985 | Cochran |
| 4,627,445 A | 12/1986 | Anderson |
| 4,657,138 A | 4/1987 | Watson |
| 4,834,717 A | 5/1989 | Foster |
| 5,104,380 A | 4/1992 | Holman |
| 5,112,307 A | 5/1992 | Foster |
| 5,120,420 A | 6/1992 | Jijima |
| 5,206,147 A | 4/1993 | Hoenes |
| 5,266,179 A | 11/1993 | Nankai et al. |
| 5,424,035 A | 6/1995 | Hones |
| 5,463,467 A | 10/1995 | Baumann |
| 5,478,324 A | 12/1995 | Meyer |
| 5,522,503 A | 6/1996 | Halbich |
| 5,582,697 A | 12/1996 | Baba |
| 5,620,579 A | 4/1997 | Genshaw |

(Continued)

*Primary Examiner* — Jacob K Ackun
*Assistant Examiner* — Jenine Pagan

(57) ABSTRACT

A pocket sized diabetic kit carrying supplies that a diabetic patient will need for 24 hours includes but not limited to Lancet pen, lancets, small test strip bottle filled with test strips, blood test meter, one or more insulin types stored in a plurality of pre-filled syringes, one syringe splint or just one hard plunger, a plurality of alcohol pads, one blood plotter pad, Velcro straps and a syringe clipper. The pocket diabetic kit is compact, small and thin and can fit into a pocket so that a diabetic patient can be easily carried in the pants' pocket or other pockets without causing inconvenience or uncomfortable. The present invention also discloses ways to modify supplies including tools, medication syringes, etc.

1 Claim, 14 Drawing Sheets

(56) References Cited

U.S. PATENT DOCUMENTS

| | | | |
|---|---|---|---|
| 5,708,247 | A | 1/1998 | Alvarez-Jcaza et al. |
| 5,723,085 | A | 3/1998 | Abrams |
| 5,723,284 | A | 3/1998 | Ye |
| 5,947,935 | A | 9/1999 | Hitchins |
| 5,951,836 | A | 9/1999 | Alvarez-Jcaza et al. |
| 5,954,738 | A | 9/1999 | LeVaughn |
| 6,055,060 | A | 4/2000 | Bolduan |
| 6,059,946 | A | 5/2000 | Nankai |
| 6,067,803 | A | 5/2000 | Wolsey et al. |
| 6,224,568 | B1 | 5/2001 | Morimoto |
| 6,241,862 | B1 | 6/2001 | McAleer |
| 6,284,125 | B1 | 9/2001 | Hodges et al. |
| 6,302,855 | B1 | 10/2001 | Lav |
| 6,413,410 | B1 | 7/2002 | Hodges et al. |
| 6,451,040 | B1 | 9/2002 | Purcell |
| 6,599,406 | B1 | 7/2003 | Kawanaka |
| 6,733,655 | B1 | 5/2004 | Davies |
| D493,532 | S | 7/2004 | LeVaughn |
| 6,781,522 | B2 * | 8/2004 | Sleva .................... A61B 5/0002 340/870.1 |
| 6,911,131 | B2 | 6/2005 | Fujiwara et al. |
| 6,959,814 | B1 | 11/2005 | Hyman |
| 6,964,650 | B2 | 11/2005 | Alexandre |
| 6,986,777 | B2 | 1/2006 | Kim |
| 7,105,006 | B2 | 9/2006 | Shraga |
| 7,112,265 | B1 | 9/2006 | McAleer |
| 7,211,096 | B2 | 5/2007 | Kuhr |
| 7,232,510 | B2 | 6/2007 | Miyazaki |
| D546,216 | S | 7/2007 | Bolognesi et al. |
| 7,250,105 | B1 | 7/2007 | Alvarez-Jcaza |
| 7,311,718 | B2 | 12/2007 | Schraga |
| 7,438,694 | B2 | 10/2008 | Boozer |
| 7,468,125 | B2 | 12/2008 | Christol |
| 7,713,229 | B2 * | 5/2010 | Veit .................... G06F 19/3468 604/65 |
| 7,901,383 | B2 * | 3/2011 | Follman ............ A61B 5/14532 206/571 |
| 7,972,312 | B2 | 7/2011 | Koopman |
| 8,043,267 | B2 | 10/2011 | Nanba et al. |
| 8,196,741 | B2 | 6/2012 | Finke |
| 8,357,107 | B2 | 1/2013 | Draudt |
| 2005/0240119 | A1 | 10/2005 | Draudt |
| 2006/0006097 | A1 | 1/2006 | Peacock |
| 2007/0265511 | A1 * | 11/2007 | Renouf .................... A61F 17/00 600/319 |
| 2009/0152159 | A1 * | 6/2009 | Beeman ................ A45C 11/00 206/570 |
| 2010/0059560 | A1 * | 3/2010 | Lanum ............... A61B 19/0264 224/257 |
| 2010/0122995 | A1 | 5/2010 | Brown |
| 2010/0206751 | A1 * | 8/2010 | Wessel ............... A61B 5/14532 206/38 |
| 2012/0089051 | A1 | 4/2012 | DirkAhlgrim |

* cited by examiner

INVENTIVE DIABETIC SYSTEMS, TOOLS, KITS, AND SUPPLIES FOR BETTER DIABETIC LIVING AND MOBILITY

REFERENCE TO RELATED APPLICATIONS

This patent application claims the benefit of U.S. Provisional Application No. 61/630,934 filed on Dec. 21, 2011, the disclosure of which is incorporated herein in its entirety by reference.

BACKGROUND OF THE INVENTION

Field of the Invention

The present invention relates to a portable diabetic kit and more specifically a pocket diabetic kit that provides a user immediate access to a one-day supplies for diabetic blood glucose test and medication in a compact package which can be put in a pocket of clothing for improving diabetic patients' living quality and mobility.

Description of Related Art

There is a need to provide great freedom to carry all diabetic products in privacy, in a kit that can be placed in a pocket for about a 24+-hour safe period, more or less depending upon time, sanitation, heat levels, and upon insulin types used. A diabetic patient user can choose to have extra storage space with them like one or more: a coat, suit, bag, purse, case, etc. The present invention will store the supplies necessary for blood glucose test and treatment while keeping the kit comfortable when carried by the user and unnoticeable to others.

Typical diabetic kits are big enough to be able to carry full length syringes. Therefore, there is a need for an invention where the insulin containing vial and syringes used can be reduced in size to be placed in a smaller kit for better mobility for the users.

Furthermore, typical medication (such as insulin) vial is for multiple doses/uses. If carried out on the road without cooling, the medication inside the vial can get spoiled and wasted. Therefore, there is a need to carry medication just enough for one day or short trips by carrying the dose of medication using a syringe. However, the regular syringe is too long and inconvenient to carry. Thus, there is a need to modify the syringe length once it is filled with medication. The present invention provides tools and method to modify the length of syringes so the modified syringes can be stored inside the compact pocket diabetic kit of the present invention.

SUMMARY OF THE INVENTION

The primary object of the invention is to provide an instant access to 24 hours or slightly longer of supplies that a diabetic patient needs such as Lancet pen, lancets, test strips, blood test meter, medication—insulin, alcohol pads, etc. whenever needed outside, at work, or camping, or wherever it may be.

Another object of the invention is to provide a diabetic kit that is compact, small, thin in size and can be put in a front pocket or any pockets available on a clothing. The device once placed in the pocket should not be noticeable. The user carrying it in the pocket should feel comfortable thus their living quality and mobility can get improved.

Yet another object of the invention is to provide reduced sized diabetic supplies including medication syringe so that they can fit into the compact sized pocket diabetic kit of the present invention.

In an exemplary embodiment of the present invention, there is disclosed a primary pocket sized diabetic kit carrying supplies that a diabetic patient will need for 24 hours or slightly longer including but not limited to Lancet pen, lancets, small test strip bottle filled with test strips, blood test meter, one or more insulin types stored in a plurality of pre-filled syringes, one syringe splint or just one hard plunger, a plurality of alcohol pads, one blood plotter pad, Velcro straps, and one syringe clipper. The pocket diabetic kit is compact, small and thin and can fit into a pocket so that a diabetic patient can be easily carried in the pants' pocket or other pockets without causing inconvenience or uncomfortable. The diabetic kit pocket is approximately 4¾×3⅜ inches with a zipper for closure. The test strip bottle is smallest it can gets for holding small test strips that work with a small and thin blood glucose meter. The Lancet pen and small test strip bottle may be combined as one single unit. The syringe clipper is a tool to make storable pre-filled syringes to last about 24 hours more or less before getting out of the house as heat levels, time, sanitation can affect the quality of medication. Thus, a user does not need to carry the syringe clipper all the time.

The pocket diabetic kit may be made of materials known in the art and in any shapes, preferably in a rectangular shape. The pocket diabetic kit has an exterior surface and interior surface. The exterior surface may be made of leather, rubber, synthetic rubber, neoprene, etc. The interior surface is made of soft Velcro thus if the supplies are wrapped with hard Velcro, they can be fixed to the interior surface in an organized manner without randomly falling down on the bottom of the kit when carried in the pocket. The pocket also has a net extending over almost half of the interior surface. Medication related syringes, plungers, and other supplies may be attached (fastened) to the net. The net also provides pouch for storing any items. The pocket diabetic kit also has a swivel hook for attachments.

The pocket diabetic kit of the present invention may include a clean blood blotter protected in a clean paper file for the kit and in a clean package to open when a user need to use it. It's invaluable for blood testing clean, comfortably, and conveniently.

The diabetic kit of the present invention may include a credit card shaped blood glucose monitoring meter. It's known that a few of blood glucose meters in the marketplace can work well with the diabetic kit of the present invention. In order to fit into a preferred embodiment of a pocket diabetic kit of the present invention, the dimension of the meter is approximately 2⅞ inches long×1¼ inches wide. The meter is approximately 0.30–0.5 inch thin. The blood glucose meter of this size if not available in the marketplace can be manufactured using current technologies.

The pocket diabetic kit may further comprise a small purse to carry mainly insulin and injection needs in an extremely compact, safe, small, portable, and efficient way. This purse may be used with or without the primary kit depending upon travel, time, complementing luggage, and distance before need of all diabetic supplies. The preferred dimension of the kit is approximately 3.5 inches long and ×2.1875 inches wide with flap shut.

The pocket diabetic kit may further comprise another purse to carry extra supplies so as to not over stuff the primary kit too much when a user needs supplies for a period longer than 24 hours. The preferred dimension of the kit is approx. 4.625 inches long and 3.5 inches wide with flap shut.

The pocket diabetic kit of the present invention may include insulin pre-filled syringe(s). Due to the large and round size of the medication (insulin) vials, the medication vials can not be best stored in this small thin kit. Even for the insulin prefilled syringes they may be too long to fit into the small diabetic kit of the present invention for convenient portability. The present invention further comprises a method to convert the medication stored in the vial or the long pre-filled syringe into short and easy to carry versions. The method comprises to withdraw medication into syringes (if it's not in pre-filled version), then use a syringe clip to cut the insulin filled syringe into proper size so that it can be carried in the kit. The present invention further comprise plunger with modified tip, modified syringe barrel with side opening, syringe splint, etc. for use together with the shortened and modified insulin pre-filled syringe. Embodiments of the plunger with modified tip, syringe barrel with side opening and syringe splint, etc. will be described in more detail in the section of description of the preferred embodiment. The insulin prefilled syringe of the present invention and other medication related supplies such as plungers, syringe splint, etc. may be stored in the small purse or may be attached to the nets inside the pocket diabetic kit.

The present invention further comprises a new element which is a combination of the test strip bottle molded/added to a lancet pen. The lancet pen should be small in size that can fit into the pocket diabetic kit of the present invention.

The method of or arrangement of wiring or connecting the above electronic components and mounting them will be well known to those with ordinary skill in the electronic and mechanical arts.

The more important features of the invention have thus been outlined in order that the more detailed description that follows may be better understood and in order that the present contribution to the art may better be appreciated. Additional features of the invention will be described hereinafter and will form the subject matter of the claims that follow.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The foregoing has outlined, rather broadly, the preferred feature of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

BRIEF DESCRIPTION OF THE DRAWINGS

Other aspects, features, and advantages of the present invention will become more fully apparent from the following detailed description, the appended claim, and the accompanying drawings in which similar elements are given similar reference numerals.

DESCRIPTION OF THE PREFERRED EMBODIMENT

Figure 1:
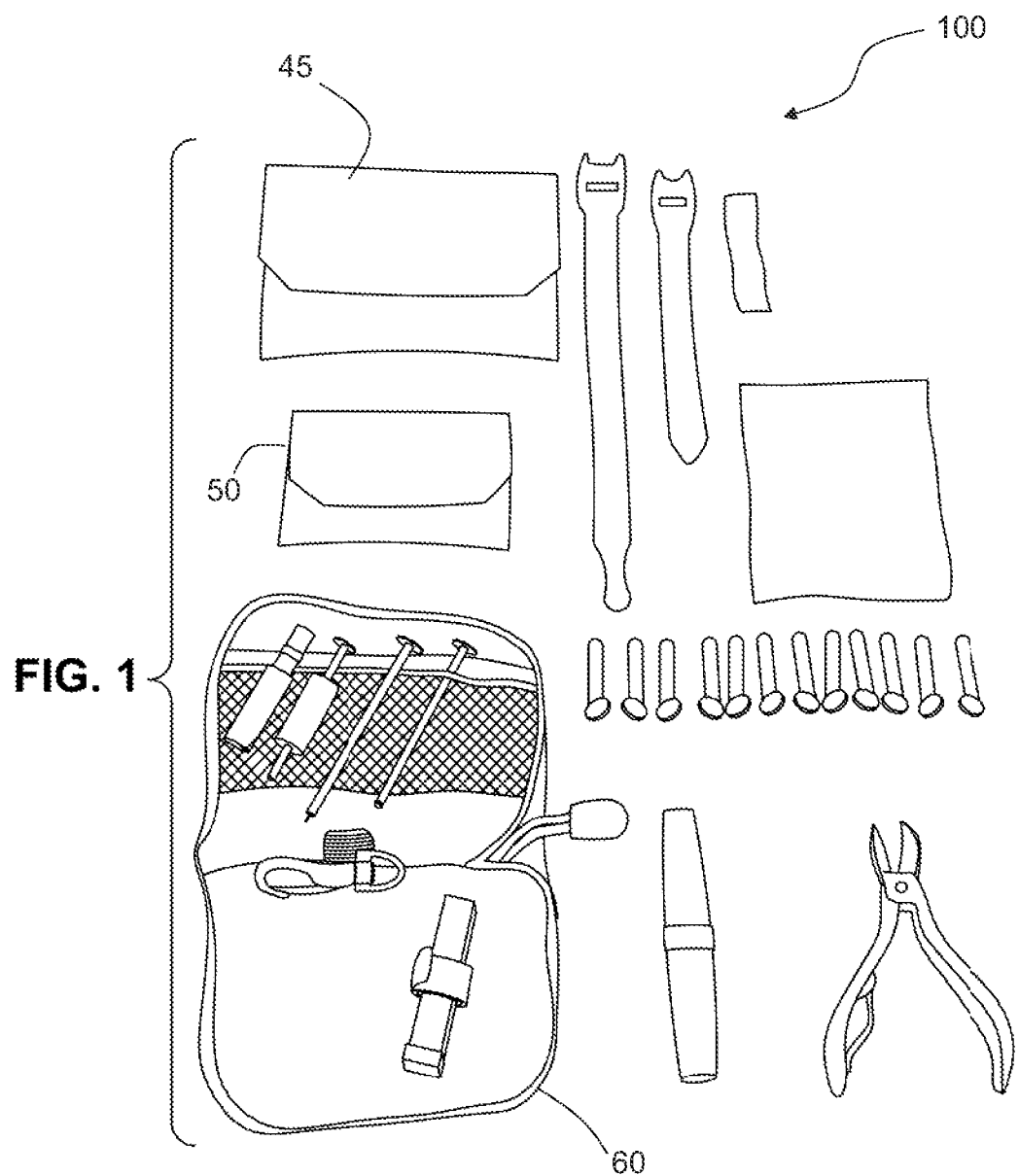
FIG. 1 is a perspective view of a pocket diabetic kit according to an embodiment of the present invention which comprises a primary pocket diabetic kit carrying 24 hours supplies for a diabetic patient, an optional small purse for storing medication related supplies, and an optional medium sized purse for storing any extra supplies.
Figure 2:
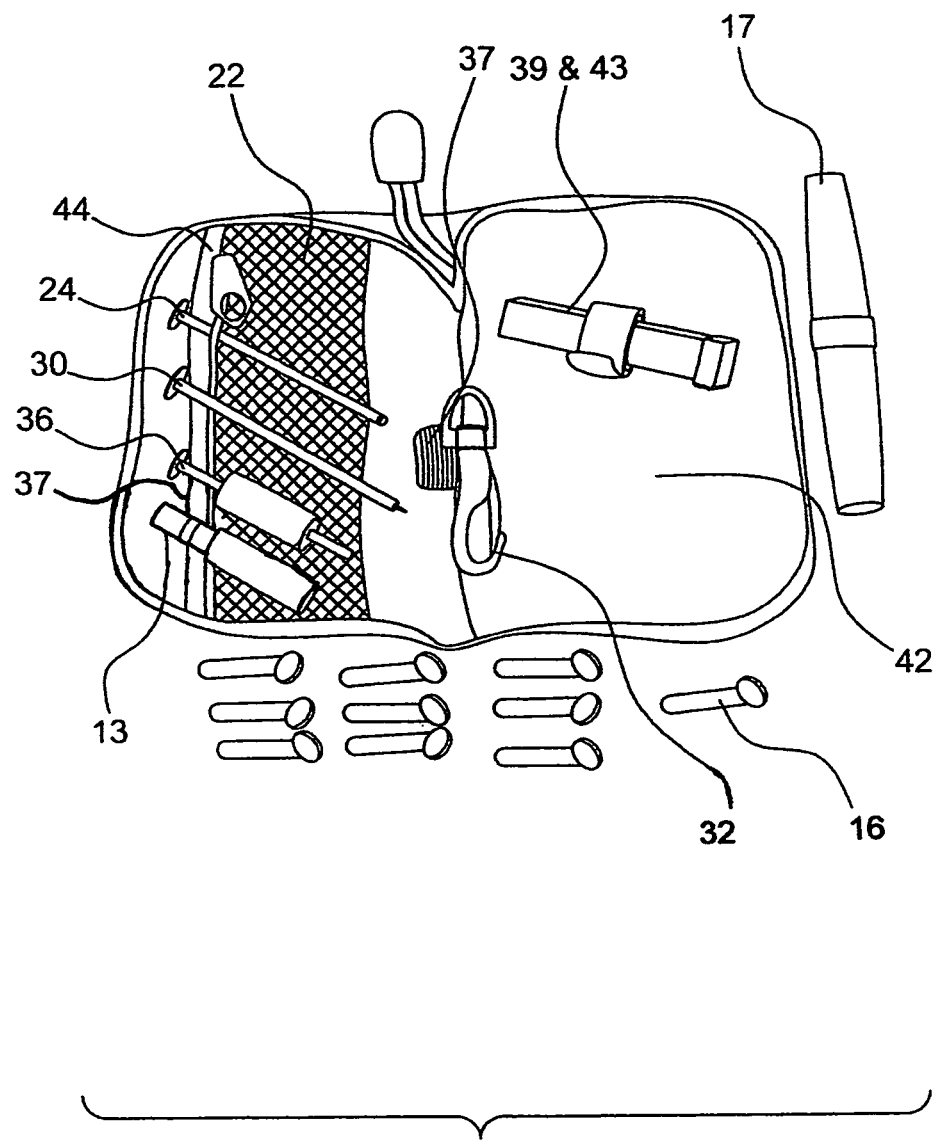
FIG. 2 is a perspective view of the primary pocket diabetic kit including 24 hours supplies for a diabetic patient according to an embodiment of the present invention.

Drawing—Reference Numbers
1. Alcohol Pad Sealed in Foil Package as found times before in stores
2. Barbed Tip Hard Plunger
3. Bottom Cover, battery, etc.
4. Bottle Melded/Added to smallest known existing lancet pen.
5. Cap Cover a
6. Cap Cover b
7. Cap Insert
8. Cut Tip Hard Plunger or Sand, Torch, Form, Friction Fit Tip by Self or Factory
9. Cut Location, Conceptual
10. Discard, Trash, or Recycle 11. Electronics
12. Front Tip
13. Insulin Bullet or Pre-filled Syringe with no hard plunger remaining and a burgundy colored cover cap as all are new ideas of creation
14. Insulin Bullet or Pre-filled Syringe with part of cut hard plunger remaining and a burgundy colored cover cap as all are new ideas of creation
15. Key Ring Card with Loop or Hole
16. Lancet
17. Lancet Pen
18. Lancet Pen Front
19. LCD Screen
20. Loop or Hole for attachment purposes
21. Medication Vial
22. Netting
23. No Side Opening, so hard plunger can be bent skillfully sideways enough to release from soft plunger with a relief cut.
24. O-Ring & Breather Tip Plunger, self made or factory made
25. Plastic Removed Flush with Battery Surface Plain
26. Removable Tape to Unseal Fresh Syringe
27. Screw On Syringe Splint or friction fit to syringe end and use 24, 30, 9, or 46 plunger
28. Side Opening, so hard plunger can be bent sideways enough to release from modified 29 soft plunger with a relief cut design.
29. Soft Plungers with a new inventive relief cut design for system bend & fast release methodology
30. Spear Tip Hard Plunger
31. Sterilized Dry Blood Blotter Pad & Storage File All Sealed in Paper
32. Swivel Hook
33. Syringe Cap
34. Syringe Clippers
35. Syringe Needle Cover Cap
36. Syringe Splint with flat cut Hard Plunger
37. Tab With Pocket Behind The Tab
38. Test Strips
39. Test Strip Bottle
40. Top Cover
41. Electronics
42. Soft Velcro Surface
43. Velcro Straps
44. Zipper Opening to Pocket Storage
45. Medium sized kit for storing extra items
46. Flat Cut Tip hard Plunger
50. Small Kit
60. Primary Purse
100. Pocket Sized Diabetic Kit Referring to FIGS. 1 and 2 there is disclosed a pocket sized diabetic kit 100 which carries supplies that a diabetic patient will need for 24 hours may include but not limited to Lancet pen 17, lancets 16, small test strip bottle 39, 4 filled with test strips (not shown) and wrapped by a Velcro strap 43 that is attached to the soft Velcro surface in the interior of the kit 42, a blood test meter (not shown), one or more insulin types stored in five to eight pre-filled syringes 13, one or more syringes splint 36 or/and with just plungers of many various types: 1) o-ring & breather tip hard plunger 24, 2) spear tip hard plunger 30, syringe, alcohol pads sealed in foil package (not shown), one blood plotter pad (not shown), and Velcro straps 43. There is also a zipper opening 44 to the pocket storage in the interior of the kit 100. The pocket diabetic is compact, small and thin and can fit into a pocket so that a diabetic patient can be easily carried in the pants' pocket or other pockets without causing inconvenience or uncomfortableness. The pocket diabetic kit 100 is approximately 4.75 inches long and 3.375 inches wide with a zipper for closure.

The pocket diabetic kit 100 comprises a primary purse 60 for storing and carrying the supplies. The primary purse 60 may be made of materials known in the art and in any shapes, preferably in a rectangular shape. The primary purse 60 has an exterior surface and interior surface. The exterior surface may be made of leather, rubber, synthetic rubber, neoprene, etc and any material known in the art that is suitable for the purpose. The interior surface is made of soft Velcro 42 thus if the supplies are wrapped with Velcro straps 43, they can be fixed to the interior surface in an organized manner without randomly falling down on the bottom of the purse when carried in the pocket. The primary purse also has a net 22 expanding over almost half of the interior surface. Medication related syringes 13, plungers 24, 30, 36, and other supplies may be attached (fastened) to the net 22 so they won't get disorganized when the kit 100 is carried in the pocket. The primary purse also has a pouch 37 for storing items such as a thinned down blood glucose meter and other items. The pouch is closed/opened by a zipper 44. The primary purse also has a swivel hook 32.

Figure 3:
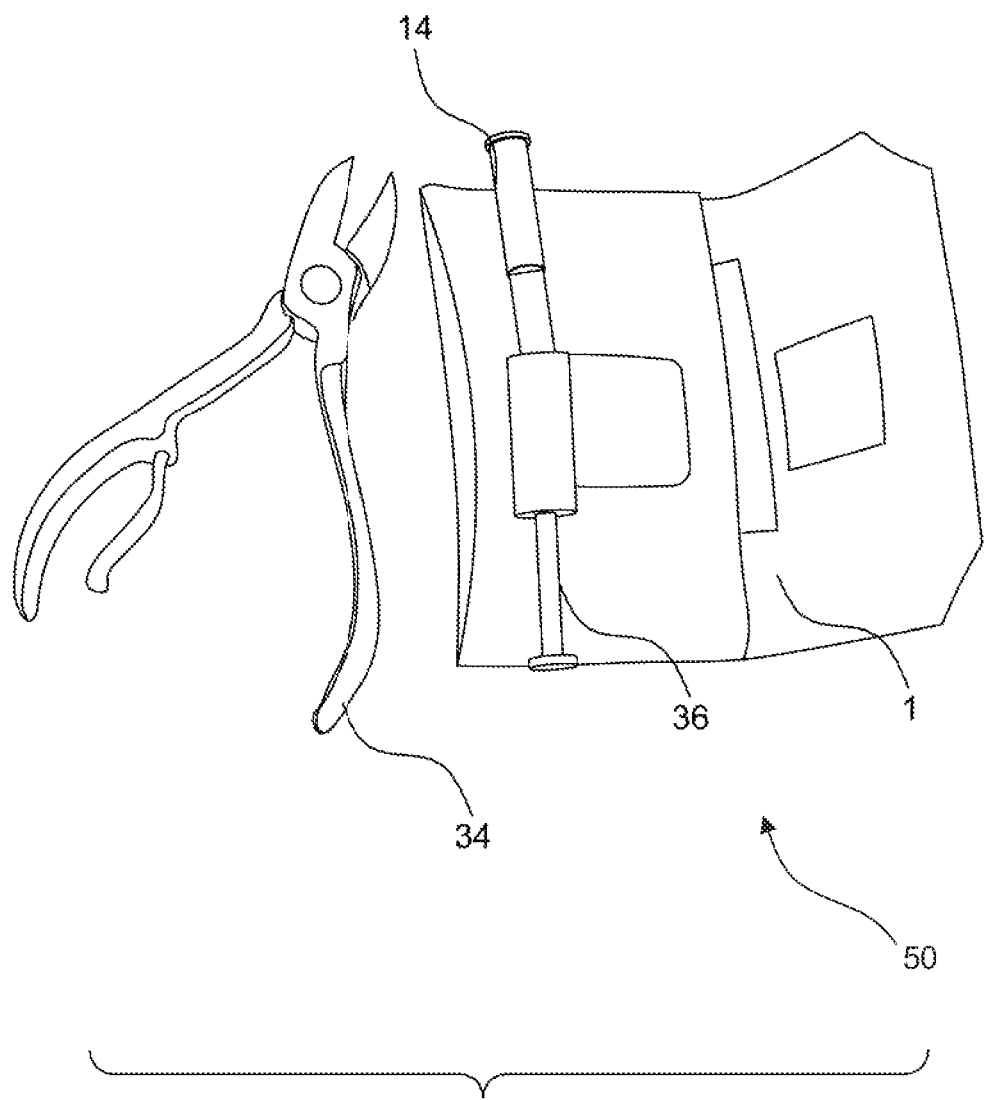
FIG. 3 is a perspective view of a small purse carrying medicine pre-filled syringes according to one embodiment of the present invention.

The pocket diabetic kit 100 may further comprise a small kit 50 (referring to FIG. 3) carrying mainly insulin bullet (not shown) or prefilled syringe with part of cut hard plunger 14 and syringe splint 36, syringe clippers 34, and other injection related items such as alcohol pad sealed in foil package 1 in a small purse in an extremely compact, safe, small, portable, and efficient way. This purse may be used with or without the primary kit 100 depending upon travel, time, complementing luggage, and distance before need of all diabetic supplies. The preferred dimension of the kit is approximately 3.5 inches long and 2.1875 inches wide with flap shut. This small kit 50 alone works well if a user tests blood sugars before leaving the home, base, or office and plans on returning a few hours after a meal. A blood glucose meter with a 0.32 inches thickness might also fit into this small kit 50 if the small kit 50 is slightly expanded in size. This small kit 50 may carry about eight pre-filled syringes of one or multiple medication types. The pre-filled syringes should have brand labeling on the cap or syringe. The purse of the small kit 50 may be made of same or different materials as that of the primary purse 60.

Figure 4:
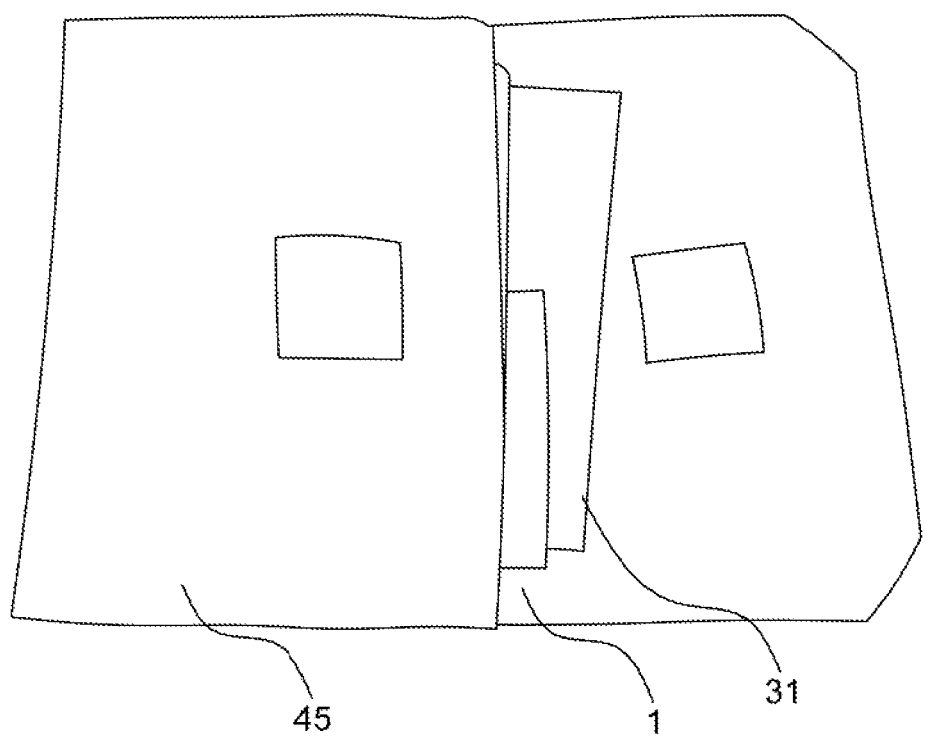
FIG. 4 is a perspective view of a medium sized purse which can carry extra supplies for a 24 hours or longer period of time in accordance with an embodiment of the present invention.

The pocket diabetic kit 100 may further comprise another purse 45 (see FIG. 4) to carry extra supplies such as sterilized dry blood blotter pad 31 and alcohol pads 1 so as to not over stuff the primary kit 100 too much when a user needs supplies for a period longer than 24 hours. The preferred dimension of the kit is approximately 4.625 inches long and 3.5 inches wide with flap shut.

The pocket diabetic kit 100 of the present invention may include a clean blood blotter protected in a clean paper file for the kit 100 and in a clean package to open when a user need to use it. It's invaluable for blood testing clean, comfortably, and conveniently.

The diabetic kit of the present invention 100 may further include a credit card shaped blood glucose monitoring meter. It's known that a few of blood glucose meters in the marketplace can work well with the diabetic kit 100 of the present invention. In order to fit into a preferred embodiment of a pocket diabetic kit of the present invention, the dimension of the meter is preferably 2.875 inches long and 1.25 inches wide. The meter is approximately 0.30–0.5 inch thin.

The blood glucose meter of this size if not available in the marketplace can be manufactured using current technologies.

The Kit 100 will well accommodate meter sizes ranging about or less than:

4.2×1.25×0.71 inches 3.5×2.2×0.58 inches 3.5×2.13×0.32 inches (this one is the thinnest known so far)

Figure 9:
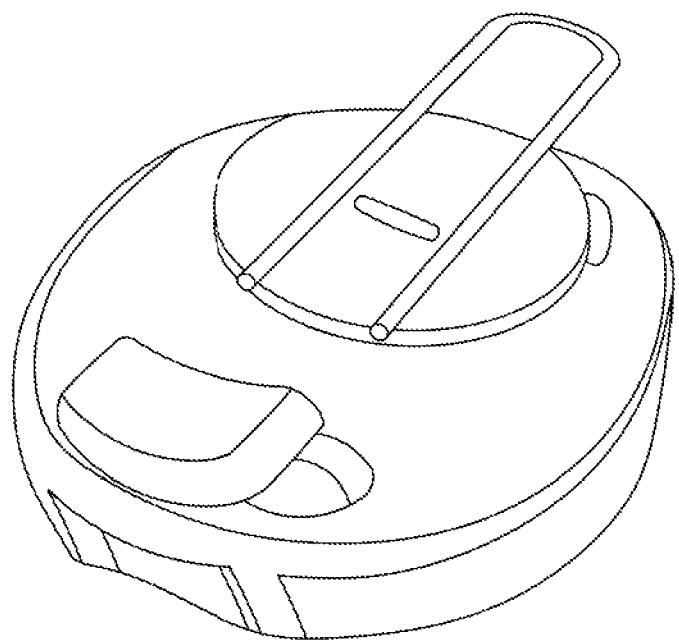
FIG. 9 is a back view of the modified blood glucose meter of FIG. 8.

1.7×1.5×0.87 inches (this one is workably thinner when made like FIG. 9 & etc.)

The Kit 100 will well accommodate Lancet Pen 17 sizes ranging about or less than:

3.7×0.58 inches 2.6×0.58 inches 4.9×0.58 inches, if the dimension of the kit 100 is changed to about 5×3⅜ inches, this size of Lancet Pen can fit into the kit 100.

The Kit 100 will well accommodate Test Strip Bottle 39 about or less than:

2.2×0.45×0.45 inches.

The pocket diabetic kit 100 may further be downsized by reducing any unnecessary material bulk, reducing zipper width, enhancing tight zipper closures, pushing out air bulk, reducing overall kit 100 size by reducing the size of suppliers, tools, meters.

Figure 5:
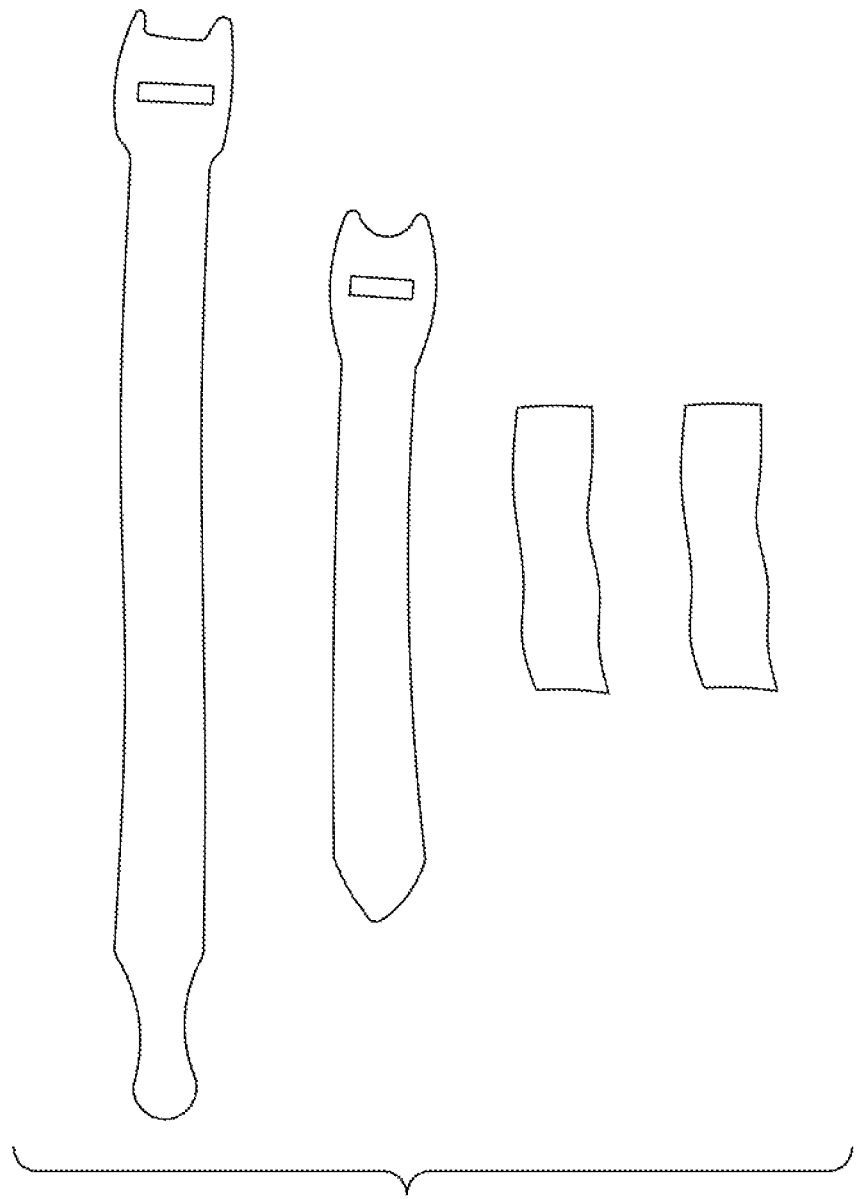
FIG. 5 is a perspective view of a couple of double sided Velcro strips.

FIG. 5 shows a plurality of double sided Velcro straps 43 available in multiple colors at fabric stores or wholesale. These straps are used to wrap things like the test meter, lancet pen, test strip bottle 39, 4, and more and then you can organize them and stick each to the soft Velcro surface 42 seen in the primary purse 60 of the pocket diabetic kit 100. This gives the kit 100 quick size adaptability to more than just one brand of blood test meter. This is a new application or system not used this way before.

Figure 6:
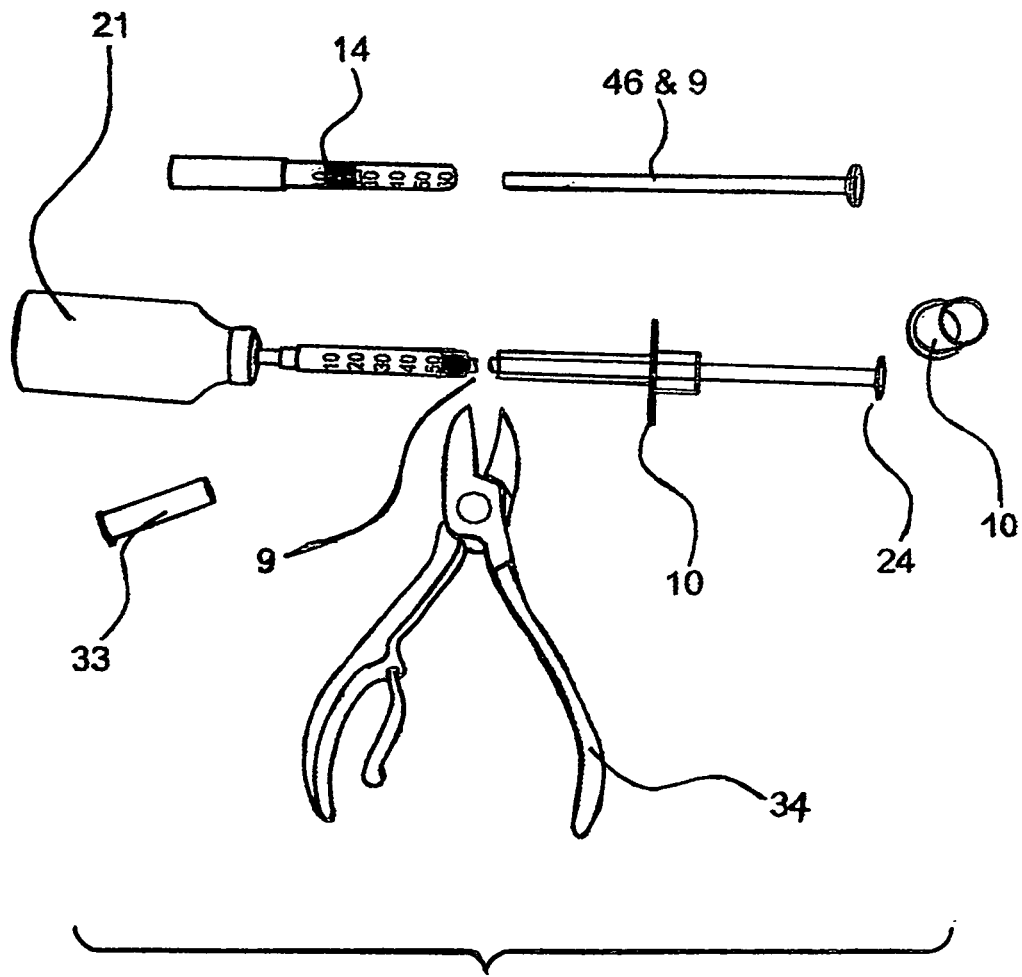
FIG. 6 is a conceptual view demonstrating how to make Insulin Bullets or short compact pre-filled syringes that can be part of the pocket diabetic kit of the present invention.

FIG. 6 demonstrates or gives understanding of how to make Insulin Bullets or short compact pre-filled syringes 13 (not shown) or 14 that can then be used with or without a Syringe Splint 36 to allow a user ability to go mobile and give the shot and inject the insulin when needed using this new system. The medication or insulin pre-filled syringe may be commercially available or prepared by using an empty syringe to withdraw medication or insulin from the medication vial 21. Many Types and sizes of medication are available in the marketplace. It is obvious that these types of vials are not suitable for the pocket diabetic kit 100 of the present invention due to shape and dimension of the vial 21. The upper syringe is made ready to go or shot ready when the o-ring & plunger tip hard plunger 24 is carefully inserted into the syringe barrel. Push out units of medication not wanted before taking the shot. Preferred are breathable snug & secure fit plungers, to when ready, push down black soft plunger. Two injection syringe parts that can be disassembled & reassembled making it possible for compact and portable storage into FIG. 3 or 2 kits. Cut syringe using syringe clip 34 when needle is still in the insulin pool and push out extra medication back into the bottle. This planned process also gives extra room to hold, rest, and insert the back end o-ring and breather tip hard plunger 24 at the time you are ready to take the shot. Once the syringe is cut at the location 9, it results in a flat cut tip hard plunger 46; trash the right side unwanted parts 10. The short compact pre-filled syringe 14, and flat cut tip hard plunger 46 together are a very simple basic workable system for portability and then eventually to injecting and taking the medication shot. The needle should be protected by the syringe cap 33 before it is placed into the kit 100. The O-ring and breather tip plunger 24 in FIG. 6 is man-made, not factory made. However it can also be factory made.

Figure 7:
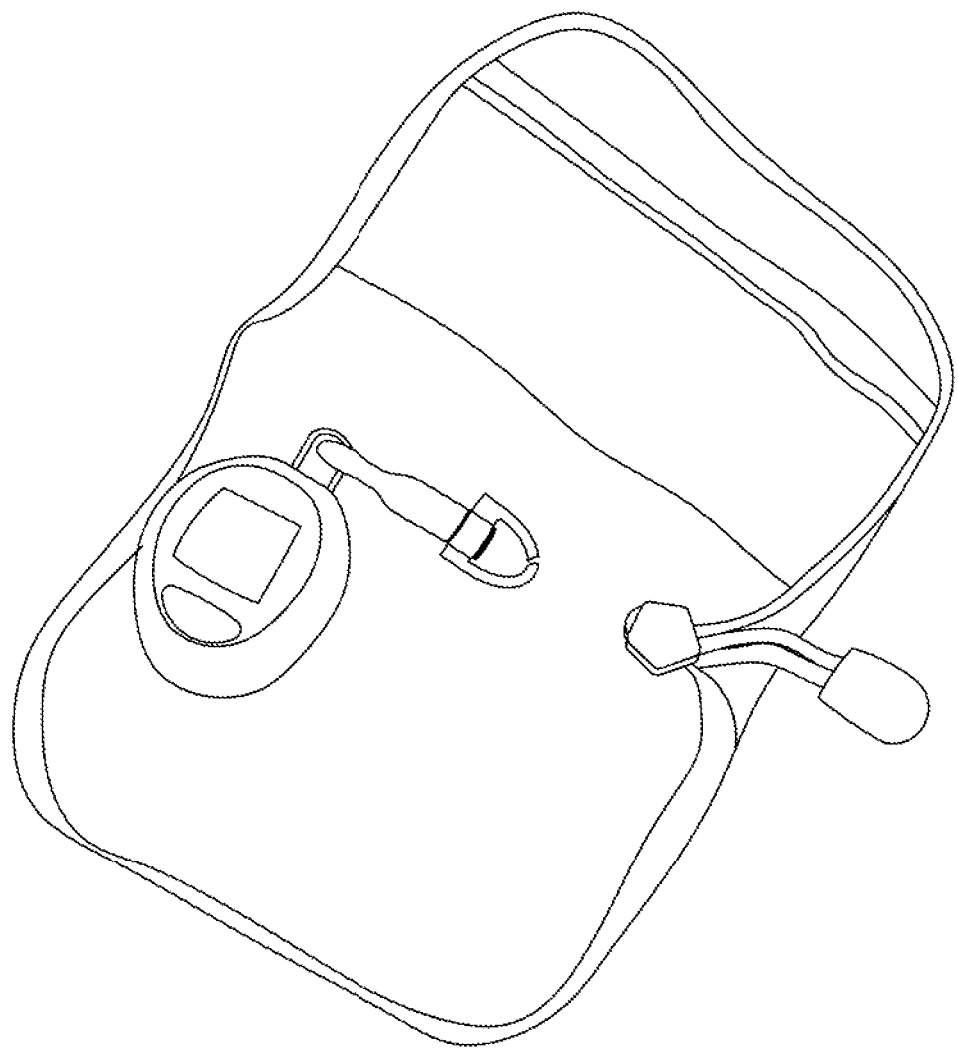
FIG. 7 is a perspective view of a thinned down blood glucose meter which can be hooked to the swivel clip inside the pocket diabetic kit and becomes part of the pocket diabetic kit.

In FIG. 7, the meter was thinned down and the meter is modified & hooked to a swivel clip system or it can hook to a key ring system to keep it attached. It's a flexible and adaptable system and no straps necessary to add thick bulk or will cover the screen when blood testing. Furthermore, it is not difficult or time consuming to attach and detach the meter. Swivel hooks 32 can be made smaller for best fit. Meters, Lancet Pens and Test Strip Bottles might at times benefit using this new clip and hook system.

Figure 8:
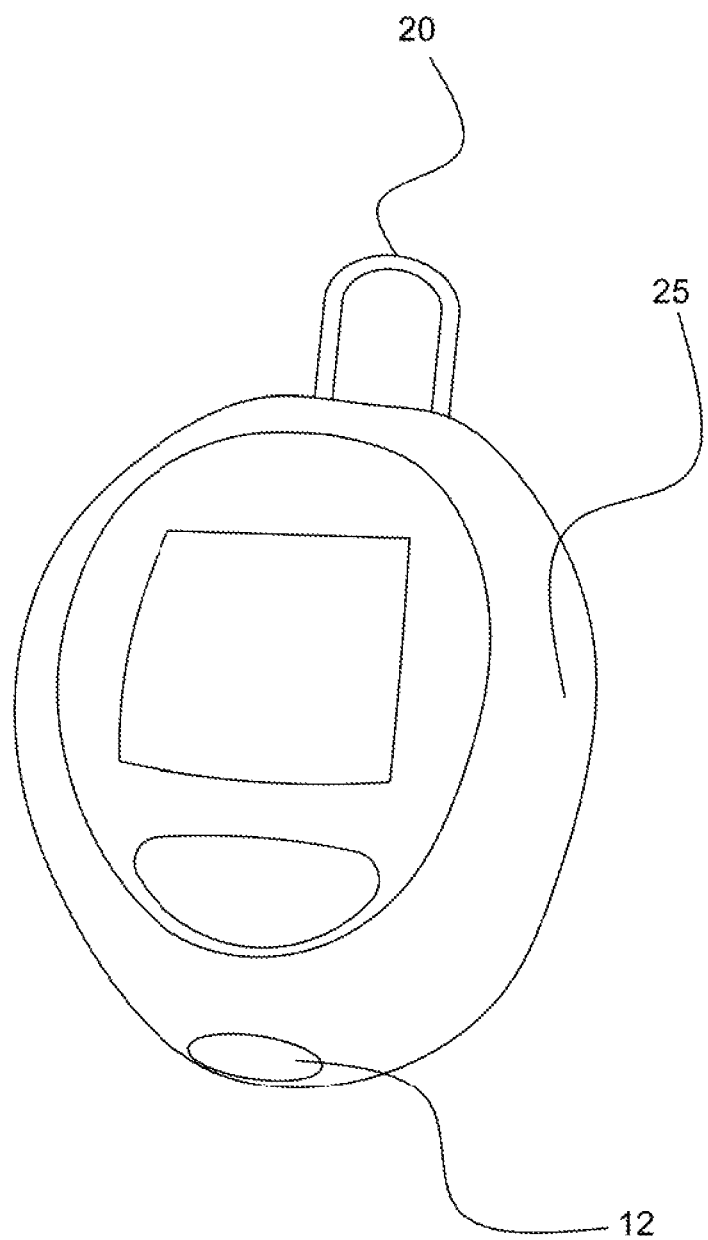
FIG. 8 is a perspective front view of a thinned down and modified blood glucose meter with a prototype hook installed according to another embodiment of the present invention.

FIG. 8 is a front perspective view of the thinned down meter with a metal or plastic hook 20 conceptually prototype installed. The plastic is removed to be flush with the battery surface plane 25. Clip meter into a kit 100 or onto a key ring. A thin flip top or pivot cover for the LCD screen, similar to the cover of a flip phone may give the screen protection and privacy from the publics' eyes. The front tip 12 of the meter has the spring removed & replaced with silicone pad or horizontal cross band to get "up push." This will allow the front tip to be flat on the back side. This design modification compresses the meter by 20%, making the meter 0.504 inches thick (making it one of the thinnest meter designs currently available) The meter may further be compressed to 0.30 inches thick in the future, which is the ideal thickness. Test Strips are sold separately in the big old fashion bottles. Only a few test strips are needed at a time for the day so the test strips should be stored in the test strip bottle 39 while traveling.

FIG. 9 is a rear view of the thinned down meter with a prototype hook 32 installed. It can be clipped onto the primary kit or onto a key ring. The excess plastic on the back of the meter is removed. This makes the meter thinner and more compact on the go or in a kit 100.

Figure 10:
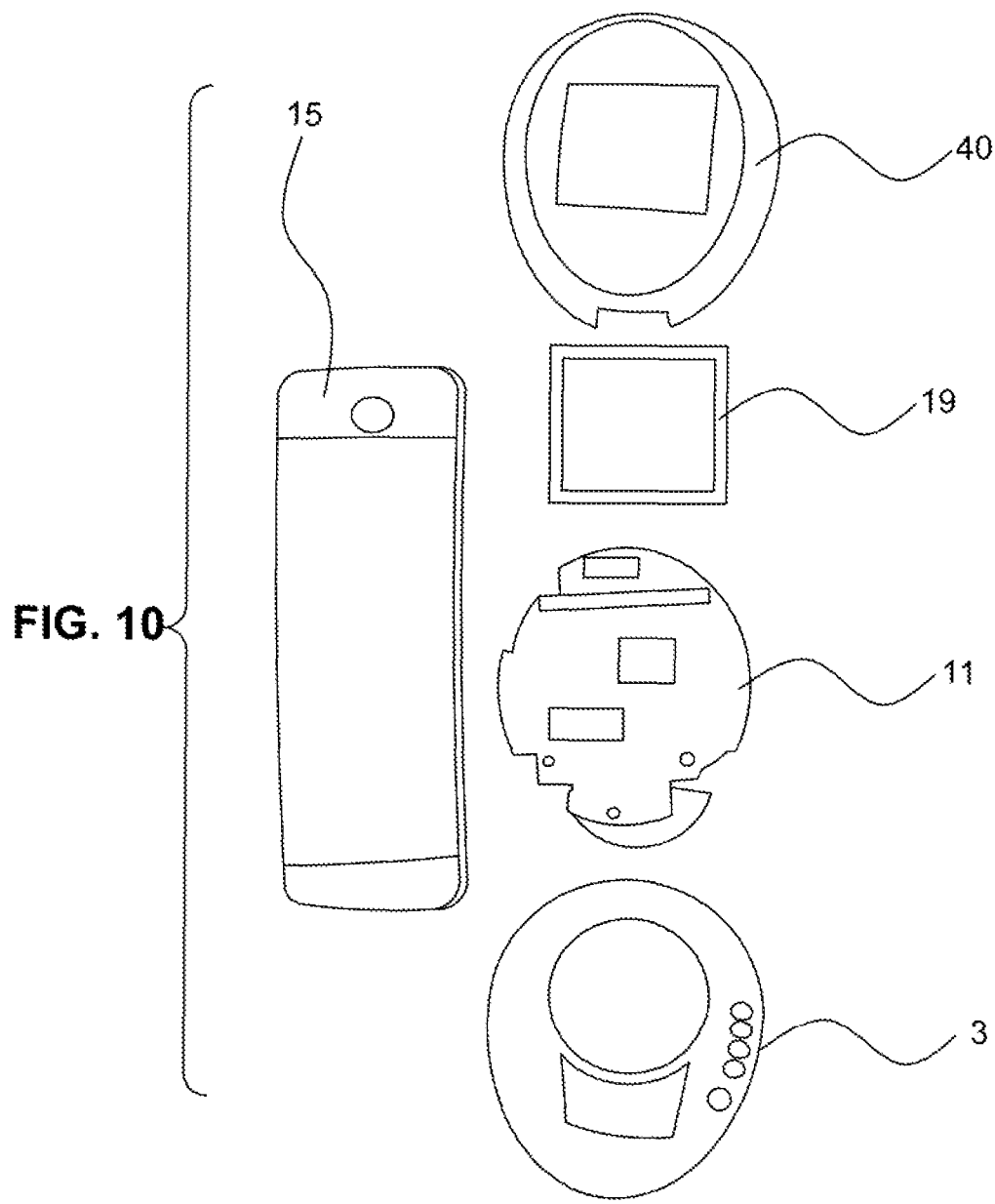
FIG. 10 is a perspective view of a key ring card shaped meter with hole or hook to attach to a key ring or to the swivel hook of the kit.

FIG. 10 is a Key Ring Card shaped Meter with hole or hook 15 to attach to a key ring or into the primary diabetic kit 100. Working with those skilled in the trade, it's possible to make it a reality. Change the meter to longer and thinner, like the key ring card with jacket bottom and top. It blends in with keys almost unnoticeable. FIG. 10 allows for kits to get smaller, because it is no longer always necessarily placed in the kit 100. An ideal location to put the meter is in the pant pocket. If placed in the pant pocket also occupied by keys, it will not even be noticeable that the pocket is also holding a meter. The meter doesn't have to be a standalone device. It may also be incorporate into cell phones, tablets, laptops, or other LCD screen 19 devices that people carry with them using known technology in the arts. The meter part sizes are seen small enough or scale down reduction all to accomplish this. The meter comprises a top cover 40 (it can be made thinner, 30+% design compression), LCD screen 19, electronics 11, and bottom cover+battery 3.

Figure 11:
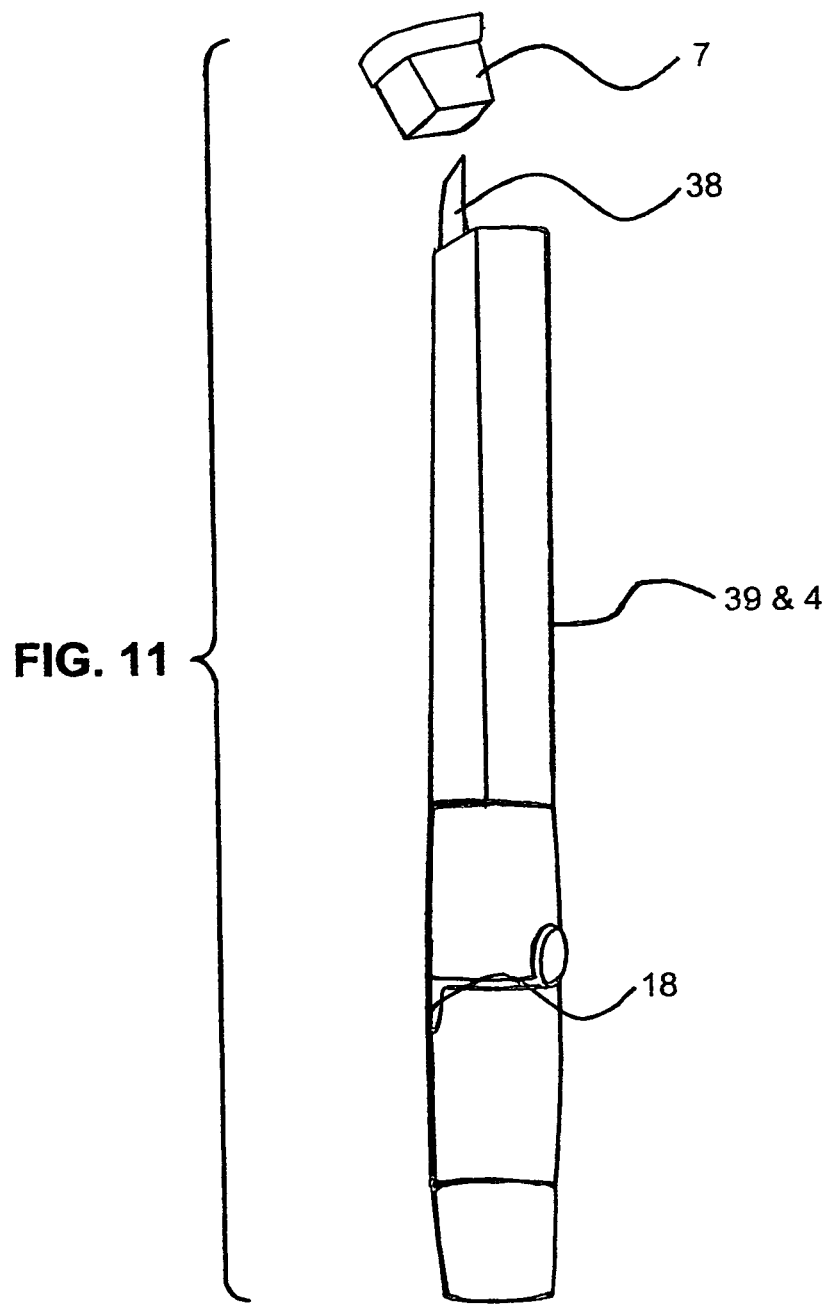
FIG. 11 is a perspective view of the lancet pen with a small test strip bottle molded as a single unit according to the present invention.

FIG. 11 is a lancet pen 17 with and small test strip bottle molded/added/built into 39 & 4 to the back end of the Lancet pen 17 to hold about 8–10 test strips 38. Current short lancet pen 17 can be modified to be longer to solve two problems. It fits well and stays upright in a pocket like a pen. It's both a tool to lancet for blood and to hold the daily travel needs for test strips 38. FIG. 11 is perhaps best placed in the pocket instead taking up space in the kit. Every aspect of the current invention's system is to reduce bulkiness for best storage use, comfort, and adaptively independent or interdependent to serve a diabetics ever changing needs in time best chosen to an individual diabetics lifestyle, medical needs, and social needs. The cap insert 7 covers the test strip 38. No modification is necessary on the Lancet pen front 18.

Figure 12:
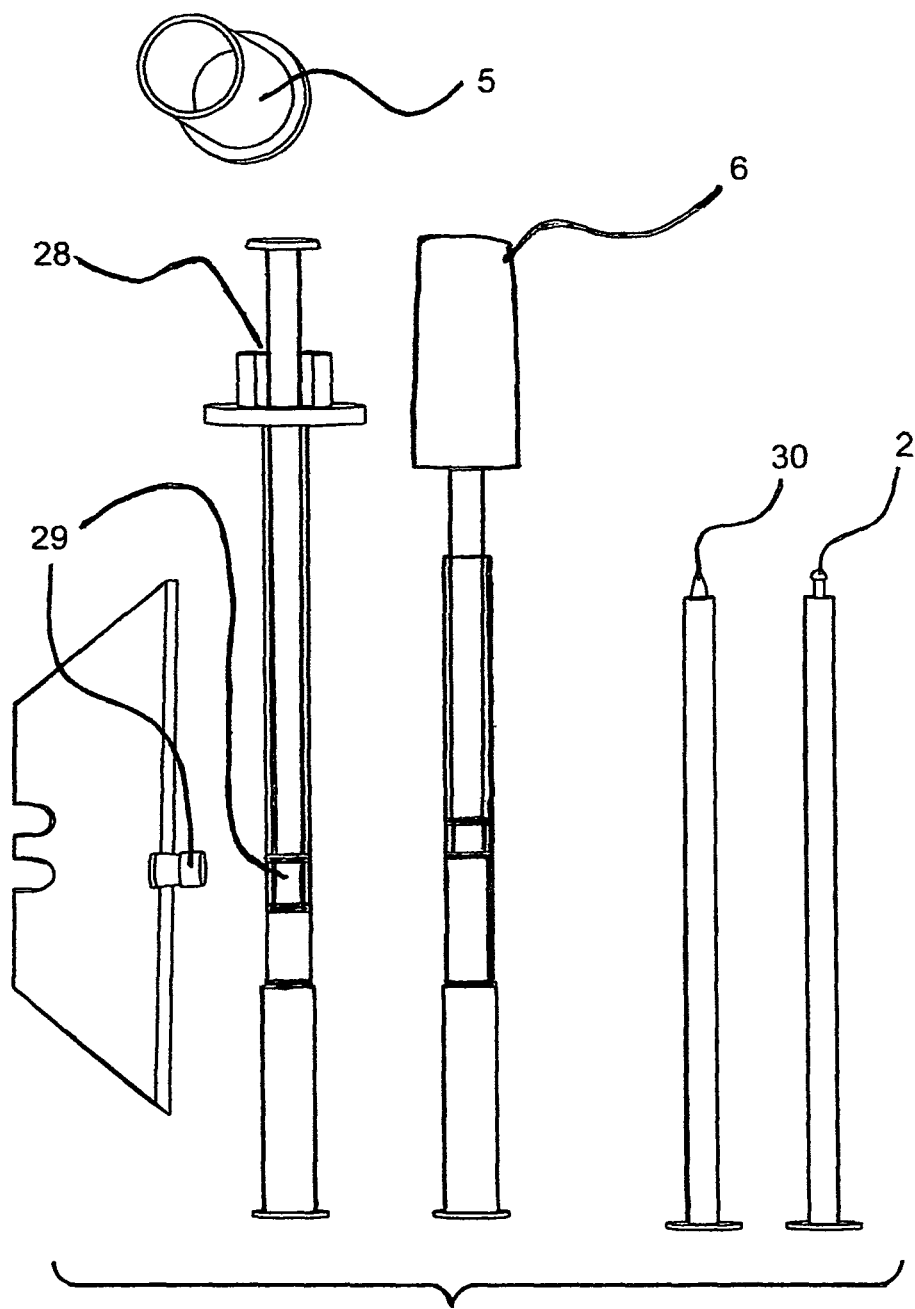
FIG. 12 is a perspective view of a couple of the new detachable hard plunger and soft plunger system that keeps all the medication inside the syringe barrel undisturbed as the hard plunger is separated at the top of the syringe barrel from the soft plunger and with no air entry caused.

FIG. 12 is a new detachable hard plunger and soft plunger system that keeps all the medication inside the syringe barrel undisturbed as the barbed hard plunger 2 is separated at the top of the syringe barrel from the soft plunger 29 without causing unwanted air entry. The pre-filled syringe is stored away for later use with no hard plunger attached 13. No syringe clipper 34 is necessary to separate the hard plungers 2 and soft plungers 29 as it is quick and simple with this method, once the soft plunger with the relief cut design 29 and the syringes are cleanly manufactured this way. Hard plunger 2 separation can only occur once black soft plunger moves a little beyond the top opening of the syringe barrel and then the hard plunger 2 is skillfully tilted sideways to be released. The removed hard plunger 2 is replaced with a compact stored and then easy twist snug fitting spear tip hard plunger 30 when a diabetic or other is ready to take the medication. Also, the cap cover-hardplunger-soft black plunger single working unit (may be made of silicone and fitted with the hard plunger, and soft black plunger) 6 like that seen in FIG. 12, is slid over the needle tip so no medication leaks occur. In other words, the barbed tip hard plunger 2, soft plungers with a new relief cut design 29, and side opening 28 is put together to form an excellent plunger release system. Then the soft plunger with relief cut 29 and spear tip hard plunger 30 replaces the barbed tip hard plunger 2 for injecting the compact mobile syringe medication when ready to be used (FIG. 12).

Figure 13:
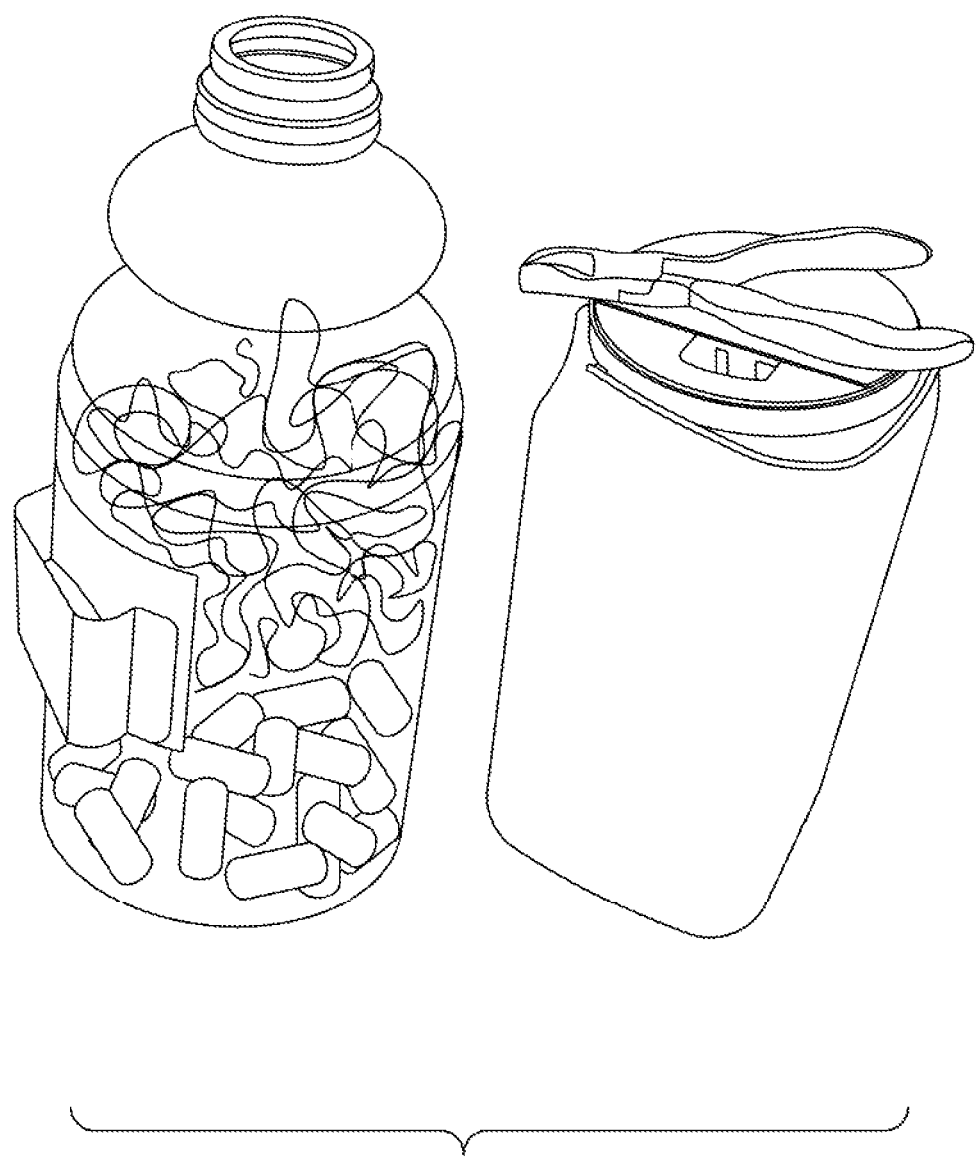
FIG. 13 is a perspective view of the syringe clipper and bottle sock privacy.

Referring to FIG. 13 there is disclosed a syringe clipper 34 and a covered syringe disposal bottle. Covering the disposal bottle provides more privacy for the user. Others that see the disposal bottle will not know its a syringe disposal bottle. The syringe clipper 34 is used to cut off the needle heads, the sharp item bottle then does not fill up as fast, saving diabetics time and money purchasing new disposal bottles. The syringe parts are not sharp, non toxic high grade plastic that can be collected and recycled.

Figure 14:
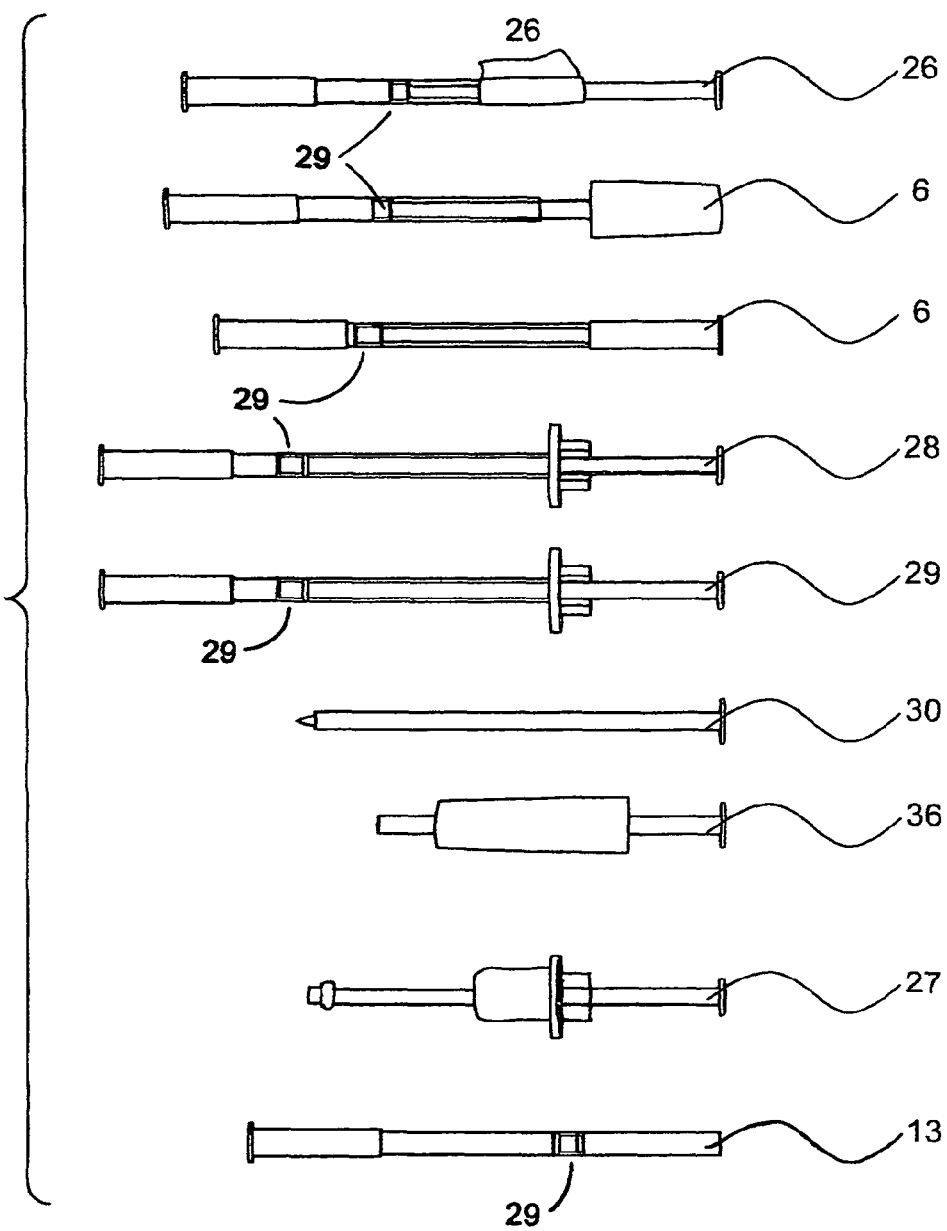
FIG. 14 is a perspective view of the various types of syringes.

Referring to FIG. 14 there is disclosed different syringes. The thin & short syringes store well. Counting syringes or items from top down, the third down (adding finger hold wings is optional) and sixth down working together as one useable system is the preferred embodiment. Syringes can also be shorter as desirable for need/use, greater or less in diameter, or as seen to best serve demanded levels of diabetic needs and/or to best fit the kits 100 for FIG. B & C or similar. Removable tape 26 may be used to unseal fresh syringe. Eliminating bulky wings on these syringes.

Another good embodiment can be seen in FIG. 6. A syringe splint with flat cut hard plunger 36 or screw on/friction fit syringe splint 27 may be used if the user prefers it. However, they are not required to get the injection job done.

The eighth down is a screw on/friction fit syringe splint 27 that fits on the syringe end and use o-ring and breather tip plunger 24, spear tip hard plunger 30, the cut location 9, or the flat cut ip hard plunger 46. When using the flat tip or if the O-Ring Tip is not used it is also possible to install silicone inside the once capped back end to make moderate friction hold hole shaft around the hard plunger shaft. The soft plungers with silicone in the back end of the syringe can also be stripped with no insulin leaks.

The fourth down has a side opening, so the hard plunger can be bent sideways enough to release from soft plungers with relief cut 29. All you really need is 14 and 46 & 9 after you cut the pre-filled syringe. If you want a real snug fit, make the o-ring & breather tip plunger 24 longer so as it breaths it doesn't compress/vacuum upon air below it's entry into the syringe. When manufacturing the o-ring & breather tip plunger 24 the syringe barrel should be manufactured with a clean beveled end for a smooth entry of the o-ring & breather tip plunger 24. Throwing away the insulin bullets 13, 14 that become unusable is not a big lost because it is only a small quantity of medication. On the other hand, if a traditional insulin vial becomes unusable due to heat exposure, etc, it is a big lost due to the greater quantity of medication.

A sterile firm & dry push on silicone in a cap 33 works well to seal a needle end so that medication do not come out or evaporate and no air entry occurs. Small fine needles not stored for long term will have no leak problems, While there have been shown and described and pointed out the fundamental novel features of the invention as applied to the preferred embodiments, it will be understood that the foregoing is considered as illustrative only of the principles of the invention and not intended to be exhaustive or to limit the invention to the precise forms disclosed. Obvious modifications or variations are possible in light of the above teachings. The embodiments discussed were chosen and described to provide the best illustration of the principles of the invention and its practical application to enable one of ordinary skill in the art to utilize the invention in various embodiments and with various modifications as are suited to the particular use contemplated All such modifications and variations are within the scope of the invention as determined by the appended claims when interpreted in accordance with the breadth to which they are entitled.

What is claimed is:
1. A pocket diabetic kit comprising:
one blood glucose meter;
one Lancet pen and a plurality of Lancets;
one portable test strip bottle having the dimension 2.2× 0.45×0.45 inches, said bottle including a plurality of test strips;
at least one pre-filled insulin syringe having a syringe barrel including a plunger comprising a piston type rod, that has a detachable rubber bulb, and at least one prefilled syringe without a piston type rod; wherein both syringes being enclosed in a sterile bag;
one syringe clipper for cutting the at least one pre-filled insulin syringe;
one primary purse for housing the blood glucose meter, Lancet pen and Lancets, test strip bottle and the test strips, the at least one pre-filled insulin syringe, and the syringe clipper;
the primary purse has a soft hook and loop fastener cloth interior surface, a swivel hook and net;
wherein the pre-filled insulin syringe can be modified by cutting the pre-filled insulin syringe shorter using the syringe clipper; and
wherein the piston type rod detaches at a cut that is formed in the said rubber bulb end of the at least one pre-filled insulin syringe having a syringe barrel including the plunger.

* * * * *